(12) United States Patent
Yamamura (10) Patent No.: US 10,321,808 B2
(45) Date of Patent: Jun. 18, 2019

(54) MANIPULATOR SYSTEM (71) Applicant: OLYMPUS CORPORATION, Tokyo (JP)

(72) Inventor: Nahoko Yamamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/596,021

(22) Filed: May 16, 2017

(65) Prior Publication Data

US 2017/0245739 A1    Aug. 31, 2017

Related U.S. Application Data

(63) Continuation of application No. PCT/JP2016/054842, filed on Feb. 19, 2016.

(30) Foreign Application Priority Data

Feb. 26, 2015    (JP) .................. 2015-036057

(51) Int. Cl.
   *A61B 1/00*   (2006.01)
   *A61B 1/04*   (2006.01)
   (Continued)

(52) U.S. Cl.
   CPC ............ *A61B 1/00133* (2013.01); *A61B 1/00* (2013.01); *A61B 1/005* (2013.01);
   (Continued)

(58) Field of Classification Search
   CPC ............ A61B 1/00147; A61B 1/00151; A61B 1/00154; A61B 1/0016; A61B 1/00009;
   (Continued)

(56) References Cited

U.S. PATENT DOCUMENTS

2009/0112060 A1   4/2009  Sugiyama et al.
2010/0022825 A1   1/2010  Yoshie
                  (Continued)

FOREIGN PATENT DOCUMENTS

EP   2052671 A1   4/2009
EP   2147630 A2   1/2010
                  (Continued)

OTHER PUBLICATIONS

International Search Report dated Apr. 26, 2016 issued in PCT/JP2016/054842.

(Continued)

*Primary Examiner* — Alexandra L Newton
(74) *Attorney, Agent, or Firm* — Scully, Scott, Murphy & Presser, P.C.

(57) ABSTRACT

Provided is a manipulator system including: a manipulator provided with an insertion section, a movable section disposed at a distal end of the insertion section, and a drive unit that is disposed at a proximal end of the insertion section and that drives the movable section; an operation input unit with which an operation input to the manipulator is input; a control unit for controlling the drive unit based on the operation input; an endoscope; an overtube having a first channel and a second channel; and a unit for calculating a shifted angle of the endoscope relative to the first channel about a longitudinal axis, wherein, on the basis of the shifted angle, the movable section is rotated relative to the second channel to match the up/down direction of a coordinate system fixed to the endoscope and the up/down direction of a coordinate system fixed to the movable section.

4 Claims, 11 Drawing Sheets

(51) Int. Cl.
  *A61B 90/00*  (2016.01)
  *A61B 1/005*  (2006.01)
  *A61B 1/018*  (2006.01)
  *A61B 34/30*  (2016.01)
  *A61B 34/37*  (2016.01)

(52) U.S. Cl.
  CPC .......... *A61B 1/00045* (2013.01); *A61B 1/018* (2013.01); *A61B 34/30* (2016.02); *A61B 34/37* (2016.02); *A61B 90/00* (2016.02); *A61B 2034/301* (2016.02)

(58) Field of Classification Search
  CPC .............. A61B 1/00135; A61B 1/0125; A61B 1/00149; A61B 1/05; A61B 1/00006; A61B 1/018; A61B 34/30; A61B 1/00133; A61B 34/37; A61B 90/361; A61B 1/04; A61B 2034/301
  See application file for complete search history.

(56) References Cited

U.S. PATENT DOCUMENTS

| | | |
|---|---|---|
| 2011/0245661 A1 | 10/2011 | Yoshie et al. |
| 2016/0007835 A1 | 1/2016 | Ogawa et al. |
| 2016/0128547 A1 | 5/2016 | Ogawa et al. |
| 2016/0354166 A1* | 12/2016 | Popovic ................. A61B 34/30 |
| 2017/0007101 A1* | 1/2017 | Dejima ..................... A61B 1/00 |
| 2017/0188792 A1* | 7/2017 | Itkowitz ............. A61B 1/00006 |

FOREIGN PATENT DOCUMENTS

| | | |
|---|---|---|
| EP | 2486846 A1 | 8/2012 |
| EP | 2997879 A1 | 3/2016 |
| EP | 3 025 629 A1 | 6/2016 |
| JP | 2000-325303 A | 11/2000 |
| JP | 2001-104333 A | 4/2001 |
| JP | 2009-101077 A | 5/2009 |
| JP | 2009-201682 A | 9/2009 |
| JP | 2010-022762 A | 2/2010 |
| JP | 2013-192803 A | 9/2013 |
| JP | 2015-024037 A | 2/2015 |
| WO | WO 2011/0432234 A1 | 4/2011 |
| WO | WO 2014/156217 A1 | 10/2014 |
| WO | 2015/012163 A1 | 1/2015 |

OTHER PUBLICATIONS

Extended Supplementary European Search Report dated Oct. 16, 2018 in European Patent Application No. 16 75 5359.3.

* cited by examiner

MANIPULATOR SYSTEM

CROSS-REFERENCE TO RELATED APPLICATIONS

This is a continuation of International Application PCT/JP2016/054842, with an international filing date of Feb. 19, 2016, which is hereby incorporated by reference herein in its entirety. This application claims the benefit of Japanese Patent Application No. 2015-036057, the content of which is incorporated herein by reference.

TECHNICAL FIELD

The present invention relates to a manipulator system.

BACKGROUND ART

There is a known endoscopic treatment system in which an electrically driven treatment tool is inserted into a channel of an overtube mounted on an endoscope, and then information on the position/orientation of the endoscope and information on the position/orientation of the electrically driven treatment tool are acquired by using sensors provided on the treatment tool and the endoscope to allow the position/orientation of the endoscope and the position/orientation of the electrically driven treatment tool to be controlled independently (refer to, for example, Patent Literature 1).

CITATION LIST

Patent Literature

{PTL 1}
Japanese Unexamined Patent Application, Publication No. 2010-22762

SUMMARY OF INVENTION

One aspect of the present invention is a manipulator system including: a manipulator including an elongated insertion section, a movable section that is disposed at a distal end of the insertion section and that has an end effector at a distal end thereof, and a drive unit that is disposed at a proximal end of the insertion section and that drives the movable section; an operation input unit with which an operation input to the manipulator is input; a control unit for controlling the drive unit on the basis of the operation input that is input with the operation input unit; an endoscope; an overtube having a first channel through which the endoscope is made to pass and a second channel through which the manipulator is made to pass; and an endoscope-rotational-angle calculation unit for calculating, on the basis of the position of the movable section in an image acquired with the endoscope, a shifted angle of the endoscope relative to the first channel about a longitudinal axis, wherein the up/down direction of a coordinate system fixed to the endoscope and the up/down direction of a coordinate system fixed to the movable section are made to match by rotating the movable section relative to the second channel about the longitudinal axis thereof on the basis of the shifted angle calculated by the endoscope-rotational-angle calculation unit.

DESCRIPTION OF EMBODIMENTS

A manipulator system 1 according to one embodiment of the present invention will now be described with reference to the drawings.

Figure 1:
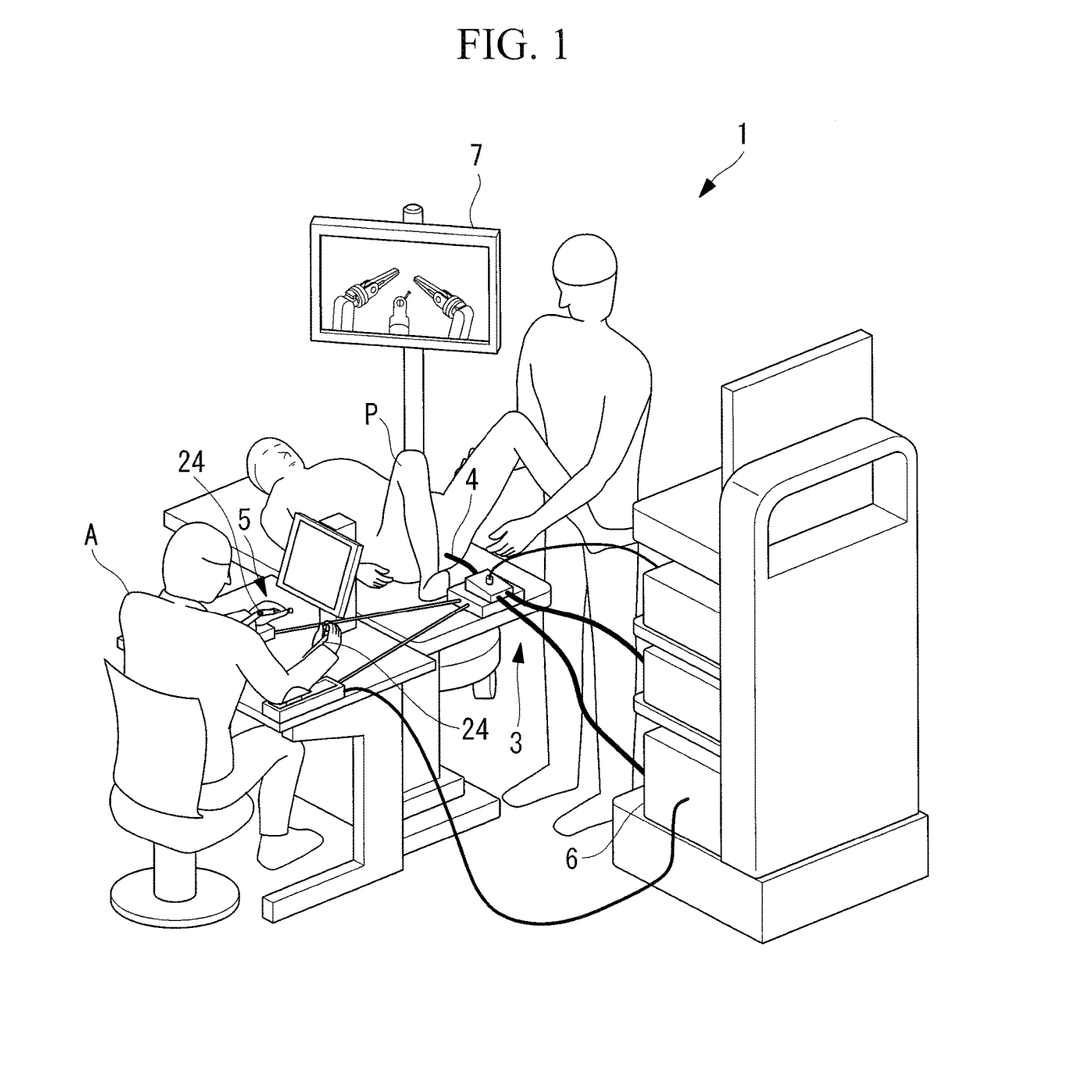
FIG. 1 is an overall configuration diagram showing a manipulator system according to one embodiment of the present invention.
Figure 2:
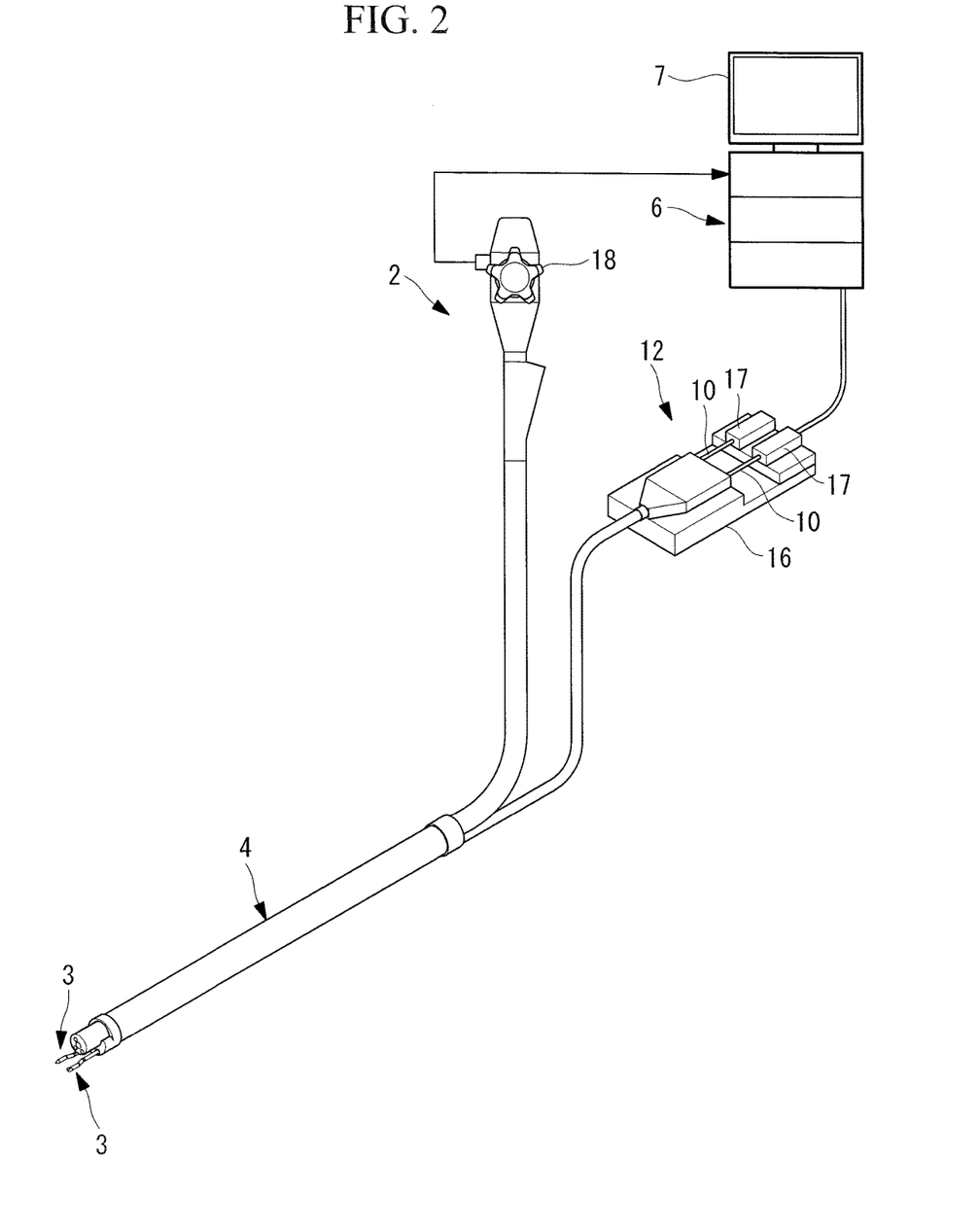
FIG. 2 is a perspective view showing the manipulator system in FIG. 1.

As shown in FIGS. 1 and 2, the manipulator system 1 according to this embodiment includes: an endoscope 2 and two manipulators 3 that are inserted into the body of a patient P; an overtube 4, according to one embodiment of the present invention, that accommodates these components; an operation input device (operation input unit) 5 that is operated by an operator A; a control unit 6 for controlling each of the manipulators 3 on the basis of the operation input that is input to this operation input device 5; and a monitor 7 for displaying an endoscopic image etc.

Figure 4:
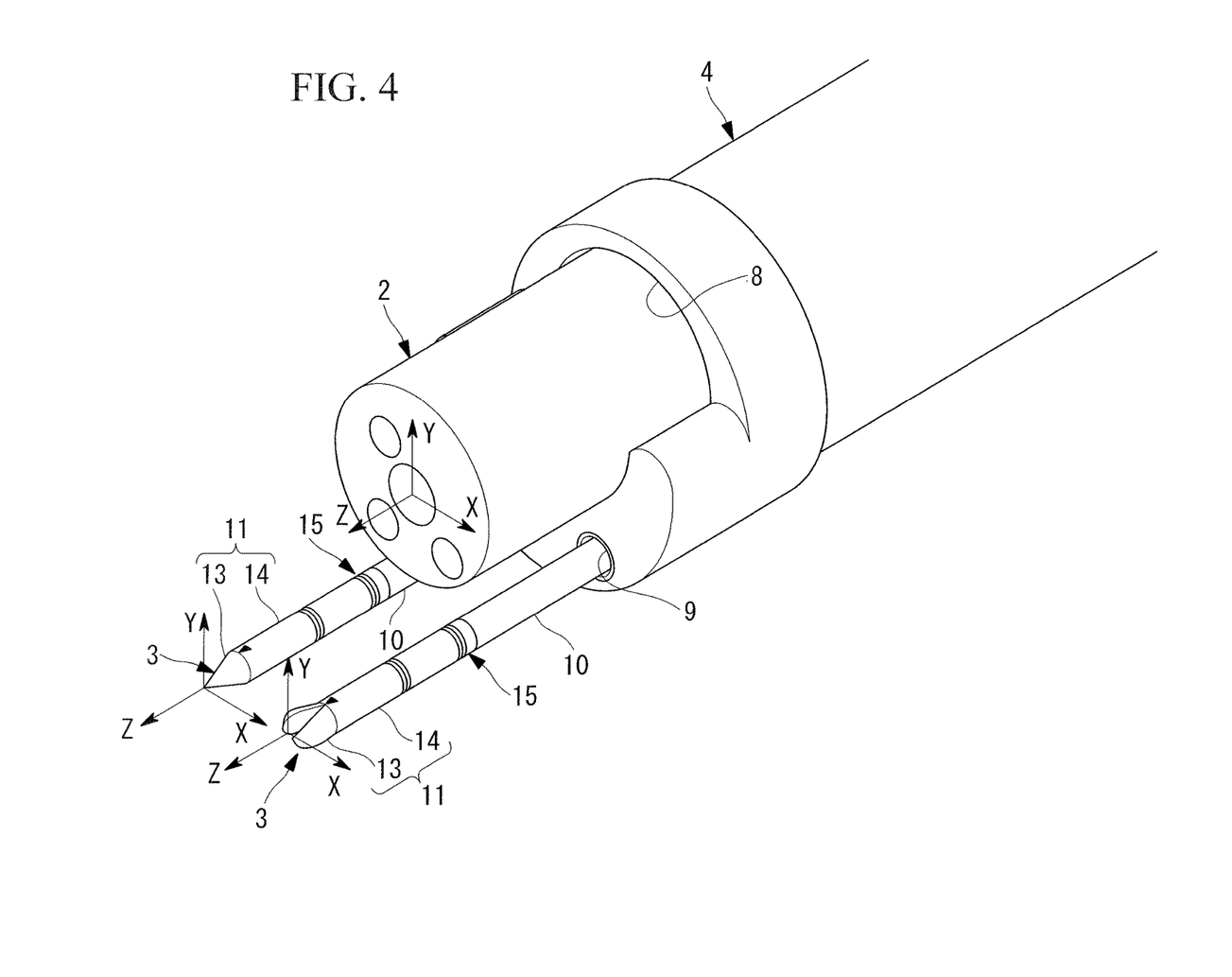
FIG. 4 is a partial perspective view showing distal ends of an endoscope, manipulators, and an overtube of the manipulator system in FIG. 3.

As shown in FIGS. 2 and 4, the manipulators 3 each include: an elongated flexible insertion section 10 inserted into the body of the patient P through a channel 9 of the overtube 4, to be described later; a movable section 11 provided at a distal end of the insertion section 10; and a drive unit 12 that is provided on the proximal end side of the insertion section 10 and that drives the movable section 11 with a force transmission member, such as a wire, not shown in the figure.

The movable section 11 includes: a treatment section (end effector) 13 that is disposed at the most distal end and that works on an affected area in the body to treat the affected area; and a plurality of joints 14 for changing the position/orientation of the distal end of the treatment section 13. In addition, on the most proximal end sides of the movable sections 11 of the manipulators 3 or on the proximal end sides of the insertion sections 10, rotational joints 15 for rotating the entire movable sections 11 about the longitudinal axes of the insertion sections 10 are provided. In FIG. 4 etc., arrow symbols shown on the movable sections 11 are for the sake of making the description clear and are not actually indicated on the movable sections 11.

As shown in FIG. 2, the drive unit 12 includes: a drive unit main body 16 provided with a motor; and manipulator-side drive units 17 that are provided detachably on this drive unit main body 16 and that transmit the driving force of the motor to the force transmission members in the insertion sections 10 when they are mounted on the drive unit main body 16.

In addition, the proximal end section of the overtube 4 is configured to be mounted detachably on the drive unit main body 16.

Figure 5A:
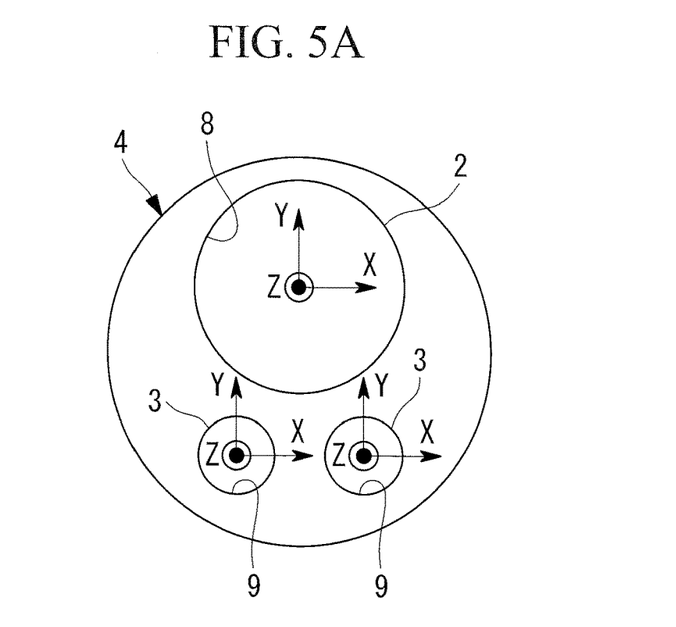
FIG. 5A is a front elevational view of the endoscope, overtube, and manipulators, showing a reference state in which the coordinate systems of the endoscope and the manipulators, which are inserted into channels of the overtube provided in the manipulator system of FIG. 1, are aligned.

As shown in FIG. 5A, the overtube 4 is a tube formed of a material having flexibility and has one first channel 8 through which the endoscope 2 passes and the two second channels 9 through which the manipulators 3 pass. The endoscope 2 inserted into the first channel 8 is configured to be able to rotate about the longitudinal axis thereof in the first channel 8. In addition, the manipulators 3 inserted into the second channels 9 are also configured to be able to rotate about the longitudinal axes thereof in the second channels 9.

As described above, the manipulator-side drive units 17 connected to the proximal ends of the insertion sections 10 and the proximal end section of the overtube 4 are mounted on the drive unit main body 16, which is installed on, for example, an operating console, and hence, angle shifts of the insertion sections 10 in the second channels 9 barely occur.

On the other hand, the proximal end side of the endoscope 2 is not fixed because it is provided with a handle 18 etc. that is grasped by the operator A to operate the endoscope 2. Thus, the position of the endoscope 2 about the longitudinal axis thereof is not fixed in the first channel 8 and is easily subjected to an angle shift.

As shown in FIG. 1, the operation input device 5 is operated with both hands of the operator A and is provided with two operating sections 24 for moving the two manipulators 3 individually. The operating sections 24 have multi-joint structures of similar or substantially similar shapes having the same axial structures as those of the manipulators 3, and each of the joints is provided with an angle sensor (angle measurement part), not shown in the figure, for detecting an angle displacement of the joint. When the operation input device 5 is operated, an angle displacement of the joint corresponding to each of the joints 14 and 15 of the manipulators 3 is detected with the angle sensor, and this detected angle displacement is sent to the control unit 6.

Figure 3:
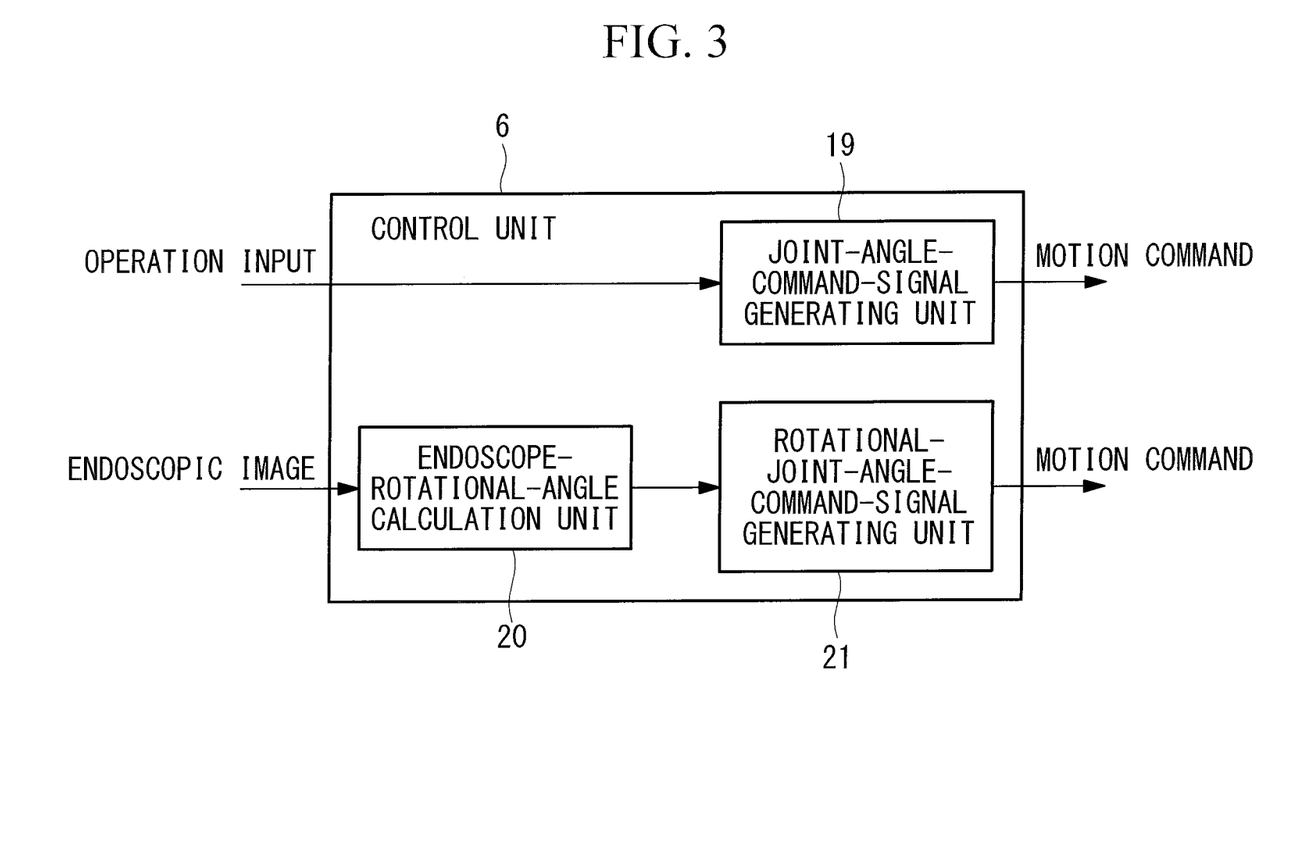
FIG. 3 is a block diagram illustrating a control unit provided in the manipulator system in FIG. 1.

As shown in FIG. 3, the control unit 6 includes: a joint-angle-command-signal generating unit 19 that receives an operation input from the two operating sections 24 and that generates a motion command, to the drive unit 12, for moving the joints 14 of the movable sections 11 of the two manipulators 3; an endoscope-rotational-angle calculation unit 20 for calculating, from an image acquired with the endoscope 2, a shifted angle of the endoscope 2 about the longitudinal axis relative to the first channel 8; and a rotational-joint-angle-command-signal generating unit 21 for generating a motion command, to the drive unit 12, for rotating each of the rotational joints 15 of the movable sections 11 of the two manipulators 3 by the shifted angle calculated by the endoscope-rotational-angle calculation unit 20.

The endoscope-rotational-angle calculation unit 20 is configured to calculate the shifted angle on the basis of the positions of the movable sections 11 of the manipulators 3 shown in an image acquired with the endoscope 2.

Figure 5B:
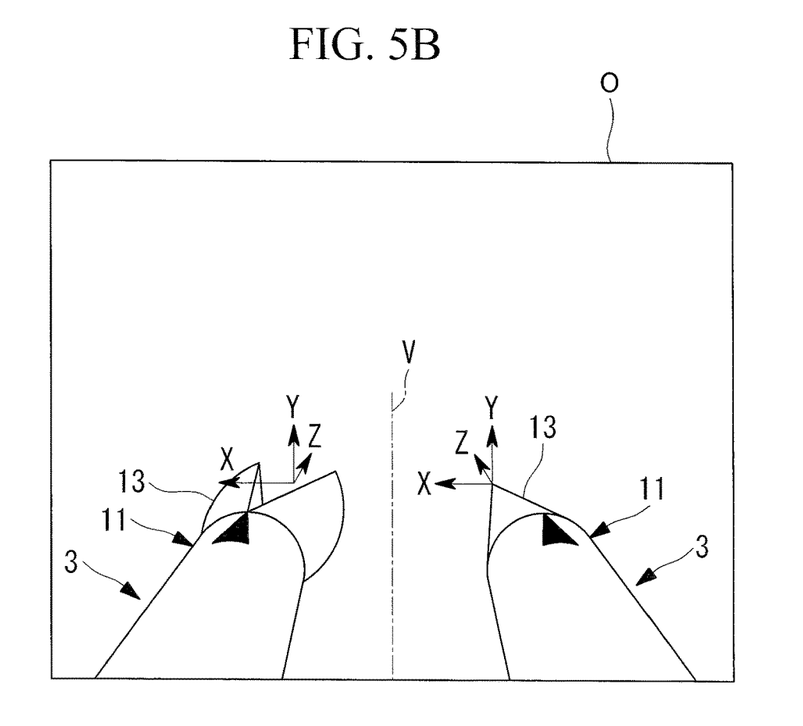
FIG. 5B is a diagram showing an example of an image acquired with the endoscope in FIG. 5A.

More specifically, as shown in FIGS. 4 and 5A, if a reference state is assumed as a state in which the coordinate system fixed to each of the endoscope 2 inserted into the first channel 8 and the manipulators 3 inserted into the second channels 9 of the overtube 4 is disposed such that the up/down direction of the coordinate system is aligned with the up/down direction of the overtube 4 (direction in which the first channel 8 is disposed on the upper side and the second channels 9 are disposed on the lower side), then an image O acquired with the endoscope 2 in this reference state is as shown in FIG. 5B.

As long as the directions of the coordinate systems of the endoscope 2 and the manipulators 3 relative to the overtube 4 are maintained in the state in FIG. 5A, the image O of FIG. 5B is acquired even if the overtube 4 rotates about the longitudinal axis.

Figure 6A:
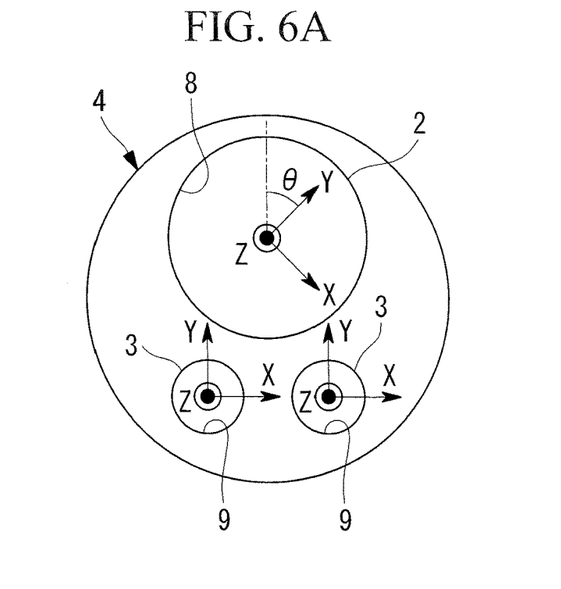
FIG. 6A is a front elevational view of the endoscope, overtube, and manipulators, showing a state in which the endoscope is rotated relative to the reference state in FIG. 5A about the longitudinal axis in a first channel of the overtube.
Figure 6B:
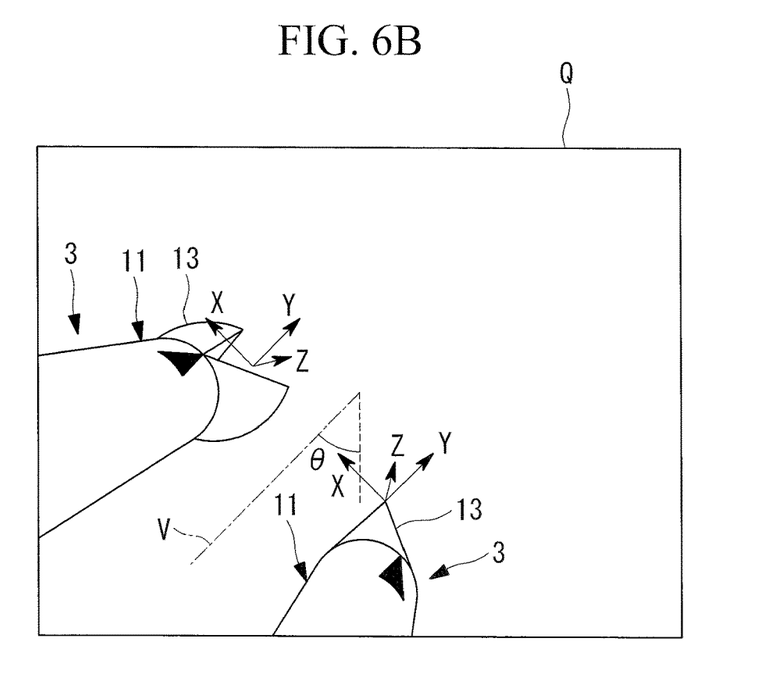
FIG. 6B is a diagram showing an example of an image acquired with the endoscope in FIG. 6A.

On the other hand, if the endoscope 2 rotates by a shifted angle θ about the longitudinal axis thereof relative to the interior of the first channel 8 as shown in FIG. 6A, then an image Q acquired with the endoscope 2 is, as shown in FIG. 6B, an image resulting from rotating the image O of FIG. 5A by the shifted angle θ. At this time, because the movable sections 11 shown in the image O change, the shifted angle θ can be calculated by calculating the amount of this change. Assuming, for example, the centerline between the two movable sections 11 in the images O and Q as a reference line V, the endoscope-rotational-angle calculation unit 20 calculates the shifted angle θ by calculating the angle of this reference line V relative to the up/down direction.

The operation of the manipulator system 1 according to this embodiment with this structure will be described below.

In order to treat an affected area of the patient P using the manipulator system 1 according to this embodiment, the insertion sections 10 of the endoscope 2 are first inserted into the first channel 8 of the overtube 4, and then the insertion sections 10 are made to protrude by a sufficient length via an opening at the distal end of the overtube 4.

While operating the endoscope 2 in this state, the insertion sections 10 are inserted into the body cavity of the patient P while the image acquired with the endoscope 2 is being confirmed.

When the distal end surface of the endoscope 2 is disposed near the affected area, and the affected area is shown in the image, the overtube 4 disposed on the proximal end sides of the insertion sections 10 of the endoscope 2 is inserted into the body cavity by moving it forward relative to the insertion sections 10 in such a manner that the overtube 4 travels along the insertion sections 10 of the endoscope 2 using the insertion sections 10 as guides.

In a state where the overtube 4 has been inserted until the distal end of the overtube 4 is disposed near the distal end of the endoscope 2, the manipulators 3 are inserted from the proximal end side of the overtube 4 into the second channels 9. No angle shifts occur easily between the overtube 4, the proximal end side of which is fixed, and the manipulators 3, the proximal end sides of which are fixed, whereas the endoscope 2, the proximal end side of which is not fixed, rotates about the longitudinal axis thereof relative to the first channel 8 of the overtube 4.

More specifically, in a normal state, the coordinate system of the endoscope 2 is not aligned with the overtube 4, unlike the diagram shown in FIG. 5A, but is shifted relative to the overtube 4, as shown in FIG. 6A.

Figure 8:
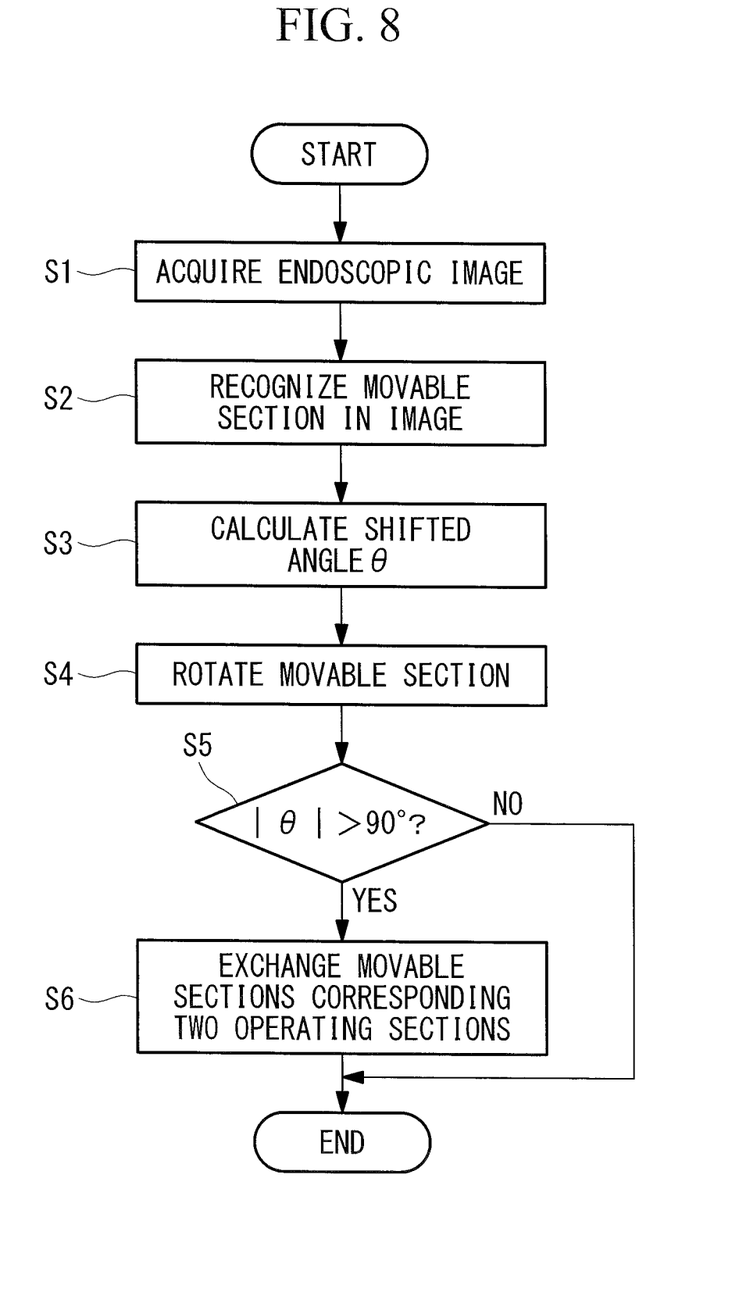
FIG. 8 is a flowchart illustrating correction processing when the endoscope is rotated about the longitudinal axis in the first channel in the manipulator system of FIG. 1.

Referring to the flowchart of FIG. 8, when the movable sections 11 of the manipulators 3 protrude forward via the openings at the distal ends of the second channels 9 and the image O showing the two movable sections 11 is acquired (step S1) as shown in FIG. 5B, the shifted angle of the endoscope 2 in the first channel 8 is calculated by the endoscope-rotational-angle calculation unit 20.

The shifted angle is calculated (step S3) by processing the image Q acquired with the endoscope 2 to recognize the movable sections 11 in the image Q (step S2), extracting a centerline between the two movable sections 11 as the reference line V, and calculating the angle of the extracted reference line V relative to the up/down direction of the image Q. In order to facilitate the recognition of the movable sections 11 in the image Q, the image Q may be binarized with the color of the movable sections 11, and the reference line V may be extracted from the acquired image.

Figure 7A:
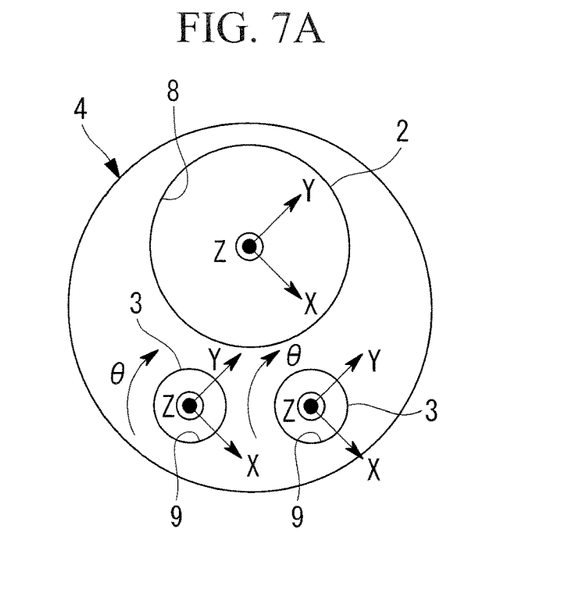
FIG. 7A is a front elevational view of the endoscope, the overtube, and the manipulators, showing a state in which the coordinate systems are aligned by rotating the manipulators in second channels by the shifted angle of the endoscope in the first channel of FIG. 6A.

After the shifted angle of the endoscope 2 has been calculated, the control unit 6 rotates each of the movable sections 11 by that shifted angle about the longitudinal axis of each of the insertion sections 10 by moving the rotational joints 15 disposed on the proximal end sides of the movable sections 11 (step S4). By doing so, as shown in FIG. 7A, the movable sections 11 rotate about the longitudinal axes of the second channels 9 of the overtube 4, so that the directions of the coordinate systems fixed to the respective two movable sections 11 are aligned with the direction of the coordinate system fixed to the endoscope 2.

Figure 7B:
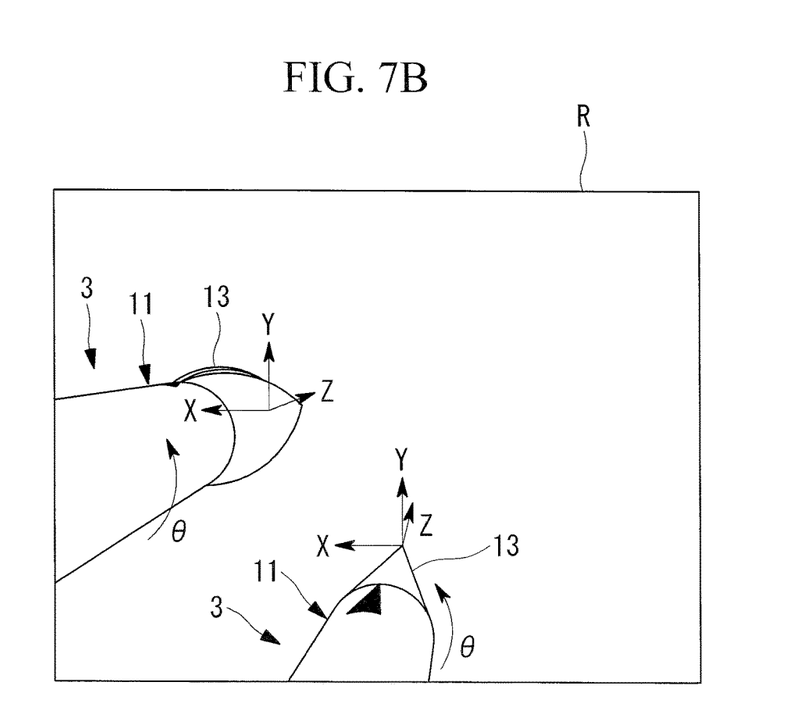
FIG. 7B is a diagram showing an example of an image acquired with the endoscope in FIG. 7A.

At this time, as shown in FIG. 7B, the movable sections 11 in an image R rotate about the respective longitudinal axes, and the up/down directions of the coordinates are made to coincide with the up/down direction of the image R.

Next, it is determined whether the absolute value of the shifted angle θ calculated by the endoscope-rotational-angle calculation unit 20 is more than 90° (step S5), and if it is more than 90°, then the correspondence relationships between the two movable sections 11 and the two operating sections 24 are exchanged (step S6). If the absolute value of the shifted angle θ is 90° or less, then the exchange of the correspondence relationships is not executed, and the movable sections 11 can be moved through the operation of the operating sections 24.

In this manner, according to the manipulator system 1 of this embodiment, the angles of the movable sections 11 are changed about the longitudinal axes thereof without barely changing the positions of the movable sections 11 in the image R, so that the up/down directions of the movable sections 11 on the image R are aligned with the up/down direction of the three-dimensional coordinate system of the operation input device 5. This makes it possible to align the operating direction in the operation input device 5 with the moving directions of the movable sections 11 on the image R, thereby making intuitive operation possible.

Figure 9A:
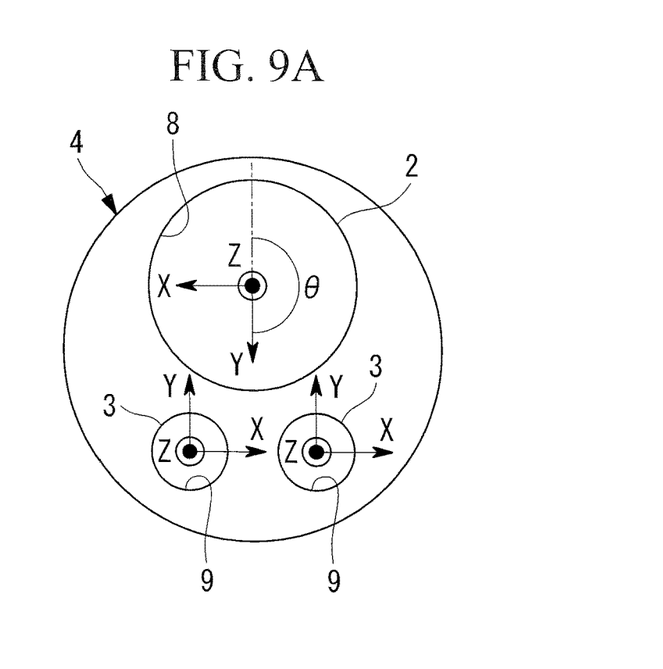
FIG. 9A is a front elevational view of the endoscope, overtube, and manipulators, showing a state in which the endoscope is rotated by 180° relative to the reference state in FIG. 5A about the longitudinal axis in the first channel of the overtube.
Figure 9B:
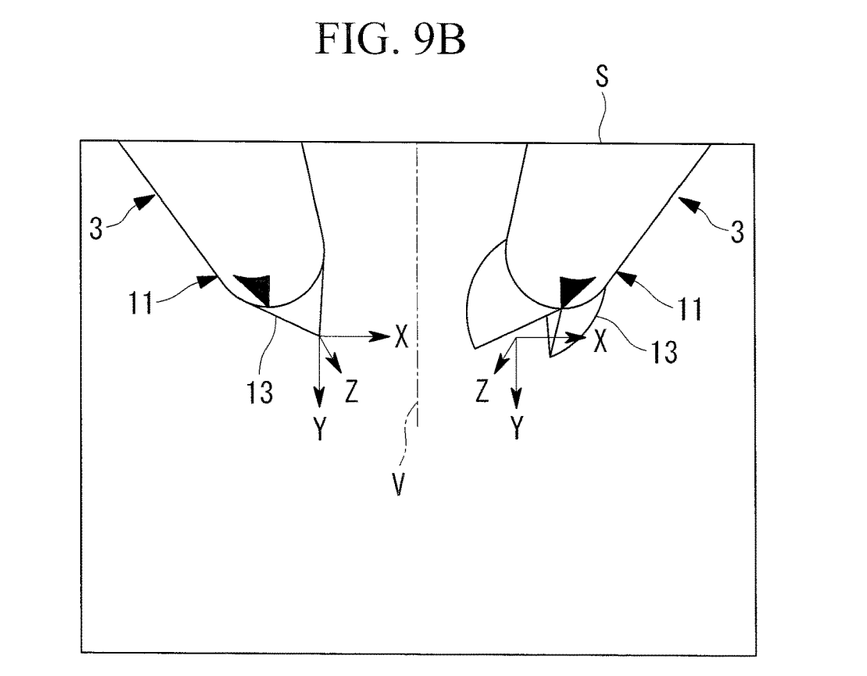
FIG. 9B is a diagram showing an example of an image acquired with the endoscope in FIG. 9A.

In addition, because the movable sections 11 are rotated by the shifted angle of the endoscope 2 calculated on the basis of the positions of the movable sections 11 in the image Q of the endoscope 2, if the shifted angle exceeds ±90°, particularly if the shifted angle approaches ±180° as shown in FIG. 9A, then the left and right directions of the movable sections 11 on an image S are exchanged, as shown in FIG. 9B, and therefore, merely correcting the up/down direction of each of the movable sections 11 is not sufficient. Here, in this embodiment, if the absolute value of the shifted angle is more than 90°, then the correspondence relationships between the two movable sections 11 and the two operating sections 24 are exchanged in step S6, thereby making it possible to operate the movable section 11 shown on the right side on the image S with the operating section 24 on the right hand side and to operate the movable section 11 shown on the left side with the operating section 24 on the left hand side. This affords an advantage in that intuitive operation is improved.

In addition, the manipulator system 1 according to this embodiment does not require processing such as the rotation of an endoscopic image for display, and this affords an advantage in that the manipulator system 1 can be configured using an existing endoscope apparatus, which does no more than acquiring, processing, and displaying images.

Figure 10:
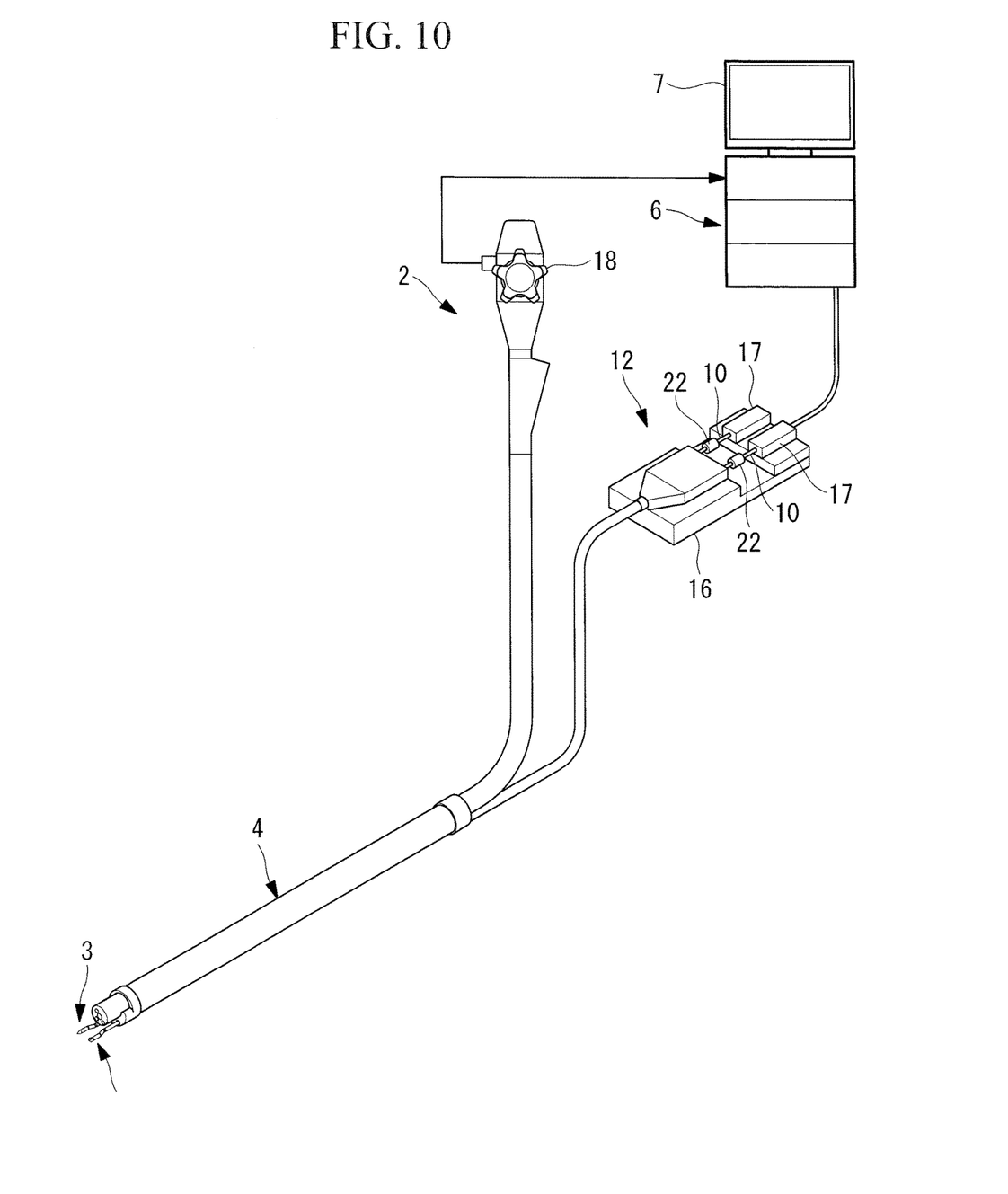
FIG. 10 is a partial perspective view showing distal ends of an endoscope, manipulators, and an overtube showing a modification of the manipulator system in FIG. 2.

In this embodiment, because the control unit 6 is provided with the endoscope-rotational-angle calculation unit 20 and rotates the movable sections 11 on the basis of a calculated shifted angle, the process of matching the coordinate systems is automatically performed when an image is acquired. Instead of this, the control unit 6 may be used solely for moving the movable sections 11 on the basis of an operation input that is input with the operation input device 5, the endoscope-rotational-angle calculation unit 20 may be provided separately from the control unit 6, and an alarm unit (not shown in the figure) for reporting the calculated shifted angle with an indication, voice, etc. may be provided. In this case, as shown in FIG. 10, it is preferable that rotational operating sections 22, such as dials, be provided on the proximal end sides of the insertion sections 10 to allow the movable sections 11 to be manually rotated about the longitudinal axes of the insertion sections 10.

Figure 11A:
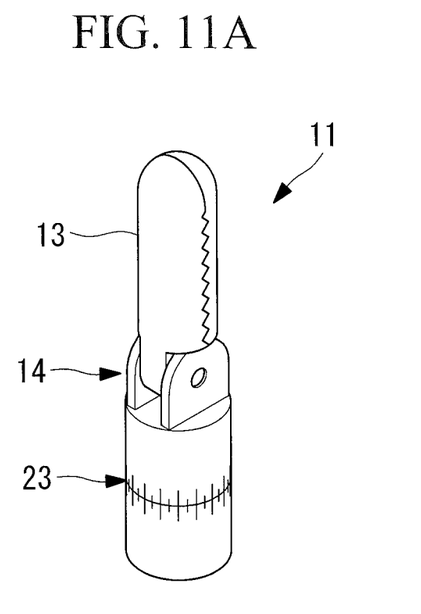
FIG. 11A is a perspective view showing a first example of a marker provided on a distal end of a movable section of the manipulator system in FIG. 1.
Figure 11B:
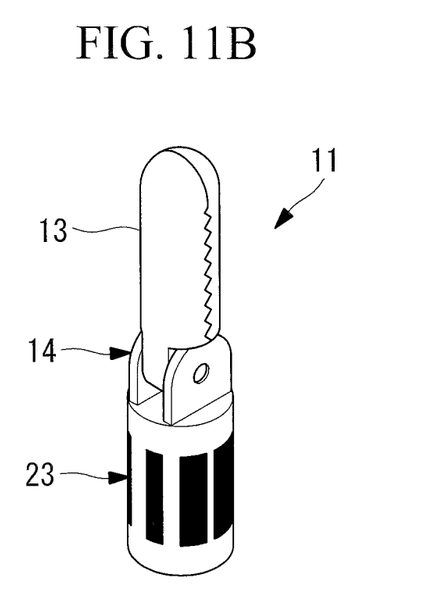
FIG. 11B is a perspective view showing a second example of a marker provided on the distal end of the movable section of the manipulator system in FIG. 1.

In addition, in this embodiment, a marker 23 as shown in FIG. 11A or 11B may be provided so that it appears near the distal ends of the movable sections 11 in an image acquired with the endoscope 2.

The marker 23 has a shape that allows the rotation of the movable sections 11 about the longitudinal axes to be identified on the endoscopic image and can be in the form of, for example, graduations arranged with spaces therebetween in the circumferential direction, as shown in FIG. 11A, or alternatively, can be in the form of, for example, marks that have different widths in the circumferential direction and that are arranged with spaces therebetween in the circumferential direction, as shown in FIG. 11B.

Rotating the movable sections 11 about the longitudinal axes relative to the second channels 9 on the basis of the shifted angle calculated by the endoscope-rotational-angle calculation unit 20 causes the up/down direction of the coordinate system fixed to the endoscope 2 to approach the up/down directions of the coordinate systems fixed to the movable sections 11 in the direction in which they coincide with each other. However, this rotation may not be transmitted to the distal ends accurately due to the rigidity of the insertion sections 10 and friction between the insertion sections 10 and the second channels 9 because the insertion sections 10 of the manipulators 3 are long. In such a case, the marker 23 shown on the image allows the actual rotational angles of the movable sections 11 to be perceived, and furthermore, the directions of the coordinate systems can be made to coincide with high accuracy by rotating the movable sections 11 using the rotational operating section 22.

In addition, although this embodiment has been described by way of an example where two manipulators 3 are provided, a single manipulator or three or more manipulators may be employed instead.

As a result, the above-described embodiment leads to the following aspects.

One aspect of the present invention is a manipulator system including: a manipulator including an elongated insertion section, a movable section that is disposed at a distal end of the insertion section and that has an end effector at a distal end thereof, and a drive unit that is disposed at a proximal end of the insertion section and that drives the movable section; an operation input unit with which an operation input to the manipulator is input; a control unit for controlling the drive unit on the basis of the operation input that is input with the operation input unit; an endoscope; an overtube having a first channel through which the endoscope is made to pass and a second channel through which the manipulator is made to pass; and an endoscope-rotational-angle calculation unit for calculating, on the basis of the position of the movable section in an image acquired with the endoscope, a shifted angle of the endoscope relative to the first channel about a longitudinal axis, wherein the up/down direction of a coordinate system fixed to the endoscope and the up/down direction of a coordinate system fixed to the movable section are made to match by rotating the movable section relative to the second channel about the longitudinal axis thereof on the basis of the shifted angle calculated by the endoscope-rotational-angle calculation unit.

According to this aspect, when the overtube having the first channel into which the endoscope is inserted and the second channel into which the manipulator is inserted is disposed in the body, the endoscope and the movable section at the manipulator distal end are protruded via openings at the distal end of the overtube, and the endoscope is operated, an image of the interior of the body is acquired and the movable section is shown in the image. The position of the movable section in the image represents the position of the second channel relative to the first channel, and if the shifted angle of the endoscope about the longitudinal axis of the first channel is zero, then the movable section appears at a predetermined position in the image. On the other hand, if the endoscope is rotated relative to the first channel about the longitudinal axis, the movable section appears at a position displaced from the predetermined position in the image.

The shifted angle of the endoscope relative to the first channel about the longitudinal axis is calculated by the endoscope-rotational-angle calculation unit on the basis of the position of the movable section in the image, and hence, rotating the movable section relative to the second channel about the longitudinal axis thereof causes the movable section to be rotated about the longitudinal axis in the image without changing the position of the movable section in the image. At this time, because the up/down direction of the coordinate system fixed to the endoscope and the up/down direction of the coordinate system fixed to the movable section are made to match, the up/down direction of the movable section in the image can be made to match the vertical direction of the operation input unit. Consequently, the operator, who operates the movable section while observing the image, can move the movable section on the basis of the coordinate system coinciding with the three-dimensional coordinate system of the operation input unit, making an intuitive operation possible.

In the above-described aspect, the control unit may cause the up/down directions of the coordinate systems to match by rotating the movable section about the longitudinal axis thereof by the shifted angle calculated by the endoscope-rotational-angle calculation unit.

By doing so, because the control unit rotates the movable section by the shifted angle when the shifted angle is calculated by the endoscope-rotational-angle calculation unit, the up/down direction of the coordinate system fixed to the endoscope and the up/down direction of the coordinate system fixed to the movable section can be made to match automatically, easily making an intuitive operation possible.

In the above-described aspect, the movable section may be provided so as to be manually rotatable relative to the second channel about the longitudinal axis thereof, an angle measurement part capable of measuring a rotational angle of the movable section relative to the second channel may be provided, and an alarm unit for reporting the shifted angle calculated by the endoscope-rotational-angle calculation unit may be provided.

By doing so, because the shifted angle is reported through the operation of the alarm unit when the shifted angle is calculated by the endoscope-rotational-angle calculation unit, the up/down direction of the coordinate system fixed to the endoscope and the up/down direction of the coordinate system fixed to the movable section can be made to match when the operator manually rotates the movable section relative to the second channel about the longitudinal axis, thus easily making intuitive operation possible. Once the endoscope is inserted into the first channel of the overtube disposed in the body cavity, the endoscope barely rotates relative to the first channel while treatment is in progress with the movable section, and therefore, manually aligning the coordinate systems once allows the subsequent treatment to be executed intuitively.

In the above-described aspect, the movable section may include, at a position thereof the image of which is acquired with the endoscope, a marker that allows the angle of the movable section about the longitudinal axis relative to the second channel to be identified in the image acquired with the endoscope.

Even if no markers are provided, rotating the movable section relative to the second channel about the longitudinal axis on the basis of the shifted angle calculated by the endoscope-rotational-angle calculation unit causes the up/down direction of the coordinate system fixed to the endoscope and the up/down direction of the coordinate system fixed to the movable section to be made to approach in the direction in which they are aligned. However, there is risk that accurate alignment is not achieved due to the rigidity of the insertion section of the manipulator and friction between the insertion section and the second channel. By doing so, the movable section can be rotated until the coordinate systems are accurately aligned with each other by referring to the marker displayed in the image, thereby making it possible to accurately align the directions of the coordinate systems with each other.

The present invention affords an advantage in that the manipulator can be operated intuitively, regardless of the relative angle between the overtube and the endoscope when the endoscope is inserted, without having to provide a special sensor on the endoscope.

REFERENCE SIGNS LIST

1 Manipulator system
2 Endoscope

3 Manipulator
4 Overtube
5 Operation input device (operation input unit)
6 Control unit
8 First channel
9 Second channel
10 Insertion section
11 Movable section
12 Drive unit
13 Treatment part (end effector)
20 Endoscope-rotational-angle calculation unit
23 Marker

The invention claimed is:

1. A manipulator system comprising:
two manipulators, each of the two manipulators including:
an elongated insertion section,
a movable section that is disposed at a distal end of the insertion section, the movable section having an end effector at a distal end thereof, and
a driver disposed at a proximal end of the insertion section that drives the movable section;
an endoscope;
an overtube having a first channel through which the endoscope is made to pass and two second channels through which the respective two manipulators are made to pass, the two second channels being provided on a chord of an outer circumference circle of the overtube;
two operating sections corresponding to the respective two manipulators; and
a controller comprising hardware, the controller being configured to:
calculate, on the basis of the position of the movable section in an image acquired with the endoscope, a shifted angle of the endoscope relative to the first channel about a longitudinal axis,
control the driver such that the up/down direction of a coordinate system fixed to the endoscope and the up/down direction of a coordinate system fixed to the movable section are made to match by rotating the movable section relative to the two second channels about the longitudinal axis thereof on the basis of the calculated shifted angle, and
exchange correspondence relationships between the two manipulators and the two operating sections when the calculated shifted angle is more than 90°.

2. The manipulator system according to claim 1, wherein the controller is further configured to cause the up/down directions of the coordinate systems to match by rotating the movable section about the longitudinal axis thereof by the calculated shifted angle.

3. The manipulator system according to claim 1,
wherein the movable section is provided so as to be manually rotatable relative to the two second channels about the longitudinal axis thereof, and
the controller is further configured to:
receive an angle measurement signal indicative of a rotational angle of the movable section relative to the two second channels, and
report the calculated shifted angle.

4. The manipulator system according to claim 3, wherein the movable section includes, at a position thereof the image of which is acquired with the endoscope, a marker that allows the angle of the movable section about the longitudinal axis relative to the two second channels to be identified in the image acquired with the endoscope.

* * * * *